United States Patent [19]

Moritz et al.

[11] Patent Number: 5,574,372
[45] Date of Patent: Nov. 12, 1996

[54] DIAGNOSTIC MAGNETIC RESONANCE APPARATUS HAVING A RADIO FREQUENCY SHIELD BETWEEN THE RADIO FREQUENCY ANTENNA AND THE GRADIENT COIL SYSTEM

[75] Inventors: Michael Moritz, Mistelgau; Ralph Oppelt, Uttenreuth; Wilhelm Duerr, Erlangen, all of Germany

[73] Assignee: Siemens Aktiengesellschaft, Munich, Germany

[21] Appl. No.: 374,028

[22] Filed: Jan. 18, 1995

[30] Foreign Application Priority Data

Jan. 19, 1994 [DE] Germany .......................... 44 01 464.3
Apr. 25, 1994 [DE] Germany .......................... 44 14 371.0

[51] Int. Cl.⁶ .................................................... G01R 33/28
[52] U.S. Cl. .......................... 324/318; 335/301; 324/322; 128/653.5
[58] Field of Search .................................. 324/318, 322, 324/300, 314; 335/298, 301; 128/653.5

[56] References Cited

U.S. PATENT DOCUMENTS

| | | | |
|---|---|---|---|
| 4,871,969 | 10/1989 | Roemer et al. | 324/318 |
| 4,924,184 | 5/1990 | Yoda | 324/318 |
| 5,243,286 | 9/1993 | Rzedzian | 324/318 |
| 5,367,261 | 11/1994 | Frederick | 324/318 |
| 5,396,173 | 3/1995 | Sakakura et al. | 324/318 |

FOREIGN PATENT DOCUMENTS

| | | |
|---|---|---|
| 0151726 | 8/1985 | European Pat. Off. . |
| WO91/19994 | 12/1991 | WIPO . |

*Primary Examiner*—Sandra L. O'Shea
*Assistant Examiner*—Raymond Y. Mah
*Attorney, Agent, or Firm*—Hill, Steadman & Simpson

[57] ABSTRACT

In a diagnostic magnetic resonance apparatus having an examination space, a radio-frequency antenna and a gradient coil system, the radio-frequency antenna is arranged closer to the examination space than is the gradient coil system. A radio-frequency shield arranged between the radio-frequency antenna and the gradient coil system, and has a first electrically conductive layer arrangement and a second electrically conductive layer arrangement arranged lying opposite the first arrangement, these being separated from one another by a dielectric. The layer arrangements have interconnects arranged side-by-side that are separated from one another by electrically insulating slots. The slots of the first layer arrangement are arranged offset relative to the slots in the second layer arrangement. Neighboring interconnects in at least one layer arrangement are connected to one another via bridges that conduct high-frequency currents, the bridges being arranged such that currents induced in the layer arrangement by the radio-frequency antenna can essentially flow only between the neighboring interconnects via the bridges.

7 Claims, 3 Drawing Sheets

DIAGNOSTIC MAGNETIC RESONANCE APPARATUS HAVING A RADIO FREQUENCY SHIELD BETWEEN THE RADIO FREQUENCY ANTENNA AND THE GRADIENT COIL SYSTEM

BACKGROUND OF THE INVENTION

1. Field of the Invention

The present invention is directed to a magnetic resonance apparatus of the type suitable for obtaining medical diagnostic information relating to a patient.

2. Description of the Prior Art

PCT Application WO 91/19994 discloses a diagnostic magnetic resonance apparatus having an examination space that is suitable for the acceptance for at least a part of a patient, a radio-frequency antenna for the transmission of excitation pulses into the examination space and/or for the reception of magnetic resonance signals from the examination space, and a gradient coil system for generating gradient magnetic fields in the examination space. The radio-frequency antenna is arranged closer to the examination space than is the gradient coil system, and a radio-frequency shield is arranged between the radio-frequency antenna and the gradient coil system for decoupling purposes. This radio-frequency shield has a first, electrically conductive film or foil or layer arrangement (henceforth only the term "layer" will be used herein, which encompasses the terms "film and foil"), and a second electrically conductive layer arrangement lying opposite the first arrangement, these layer arrangements being separated from one another by a dielectric. The layer arrangements have interconnects arranged, side-by-side that are separated from one another by electrically insulating slots, with the slots in the first layer arrangement arranged offset relative to the slots in the second layer arrangement.

The radio-frequency shield in this known apparatus is fashioned such that it is transmissive for the signals in the low-frequency range generated by the gradient coil system but is impermeable for the signals in the high-frequency range generated by the antenna. Such a frequency behavior is achieved by the measures disclosed as well in European Application 0 151 726. The radio-frequency shield is slotted so that the eddy currents generated in the radio-frequency shield by the gradient coil system are slight. The slots, however, reduce the shielding property of the high-frequency signals emitted by the antenna. The radio-frequency shield therefore includes the aforementioned second layer arrangement that is likewise slotted and whose slots are offset compared to the slots in the first layer arrangement. The high-frequency current generated by the antenna can now flow in a circuit which is closed by means of the capacitances that are formed in this way. Due the dielectric losses in the radio-frequency shield, however, the Q of the antennas is lowered. In particular, the whole body antenna is affected as a result because of its spatial proximity to the radio-frequency shield.

SUMMARY OF THE INVENTION

An object of the present invention is to provide a diagnostic magnetic resonance apparatus which employs a radio-frequency shield between the radio-frequency antenna and the gradient coil system wherein the dielectric losses in the radio-frequency shield are reduced in order to enhance the quality (Q) of the antenna.

This object is achieved in a diagnostic magnetic resonance apparatus wherein neighboring interconnects in at least one layer arrangement of the shield are connected to one another via bridges that conduct high-frequency currents, the bridges being arranged such that currents induced in the layer arrangement by the radio-frequency antenna essentially flow via the bridges between the neighboring interconnects. It has been shown that the transmissivity of the radio-frequency shield for the gradient fields is not significantly degraded due to the presence of the additional bridges. Moreover, the bridges result in a large part of the induced, high-frequency currents being prevented from flowing from one interconnect to the neighboring interconnect via the dielectric. The dielectrical losses are correspondingly reduced. Care must be exercised in the arrangement of the bridges to ensure that no ring currents can be induced over a plurality of interconnects, the resonant frequency of these ring currents lying in the range of the operating frequency of the diagnostic magnetic resonance apparatus.

In an embodiment, the bridges can be formed by pieces of metal foil. Proceeding from a slotted, basic embodiment, the layer arrangements can thus be matched to different antenna embodiments and antenna shapes.

In another embodiment, at least some of the bridges can be formed by capacitors. The capacitors are dimensioned such that they have a substantial resistance for the operating frequencies of the gradient coil system, whereas their resistance for operating frequencies of the radio-frequency antenna is negligible. Closed circuits for the gradient fields are thus prevented from forming in the radio-frequency shield over a plurality of interconnects.

In another embodiment, at least some of the bridges are connected to the interconnects via soldered connections. The layer arrangements can thus be easily adapted to the antenna shapes employed.

In a further embodiment, the layer arrangements together with the dielectric are implemented in the form of at least one printed circuit board, whereby at least some of the bridges are executed unitarily (i.e., in one piece) with the interconnects. Taking the bridges into consideration in the printed circuit board layout yields an economic embodiment.

Even if only one layer arrangement is provided with the bridges in accordance with the invention, the dielectric losses can still be kept especially low when this layer arrangement faces toward the radio-frequency antenna.

DESCRIPTION OF THE PREFERRED EMBODIMENTS

Figure 1:
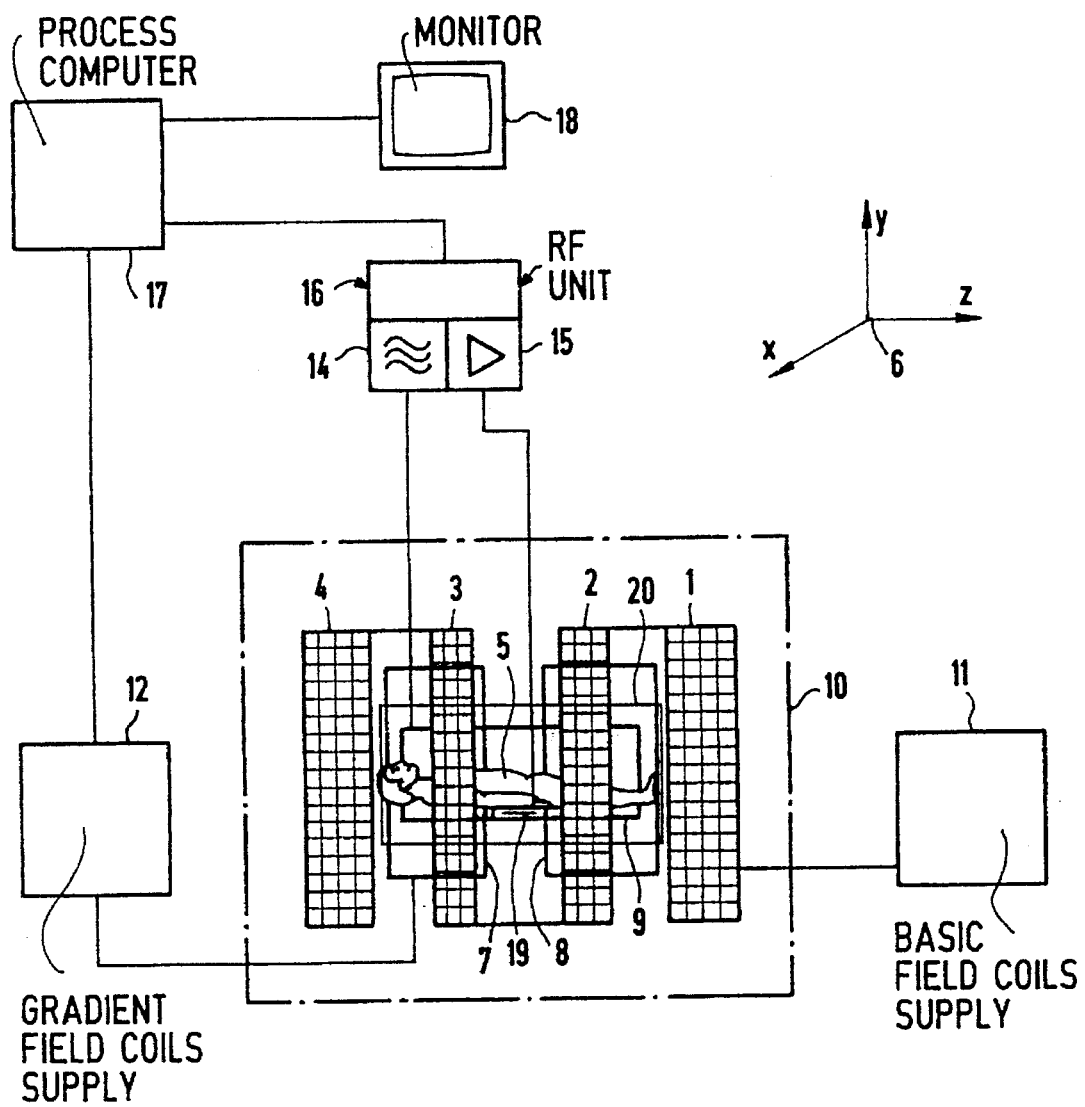
FIG. 1 is a schematic block diagram of a conventional magnetic resonance diagnostic apparatus, in which the invention can be employed.

In the known structure of a diagnostic magnetic resonance apparatus shown in FIG. 1, coils 1, 2, 3 and 4 generate a basic magnetic field $B_0$ in an examination space wherein the body 5 of a patient to be examined is located, given employment for medical diagnostics. Gradient coils are also allocated to the examination space, these being provided for generating independent, mutually perpendicular magnetic field gradients respectively the directions x, y and z according to a coordinate axis 6. For clarity, only the gradient coils 7 and 8 are referenced in FIG. 1, these serving the purpose of generating an x-gradient together with a pair of identical gradient coils that lie opposite thereto. Identical y-gradient coils (not shown) lie parallel to the body 5 above and below it. The gradient coils for generating the z-gradient field are arranged transversely relative to the longitudinal axis at the foot end and at the head end of the body 5. The arrangement also contains a whole body antenna 9 serving the purpose of generating and/or receiving nuclear magnetic resonance signals, and also contains a local antenna 19 provided only for the reception of nuclear magnetic resonance signals.

The coils 1, 2, 3, 4, 7, 8, 9 bounded by a dot-dashed line 10 represent the actual examination instrument. It is operated proceeding from an electrical arrangement that includes a power supply 11 for the operation of the coils 1–4 as well as a gradient power supply 12 to which the gradient coils 7 and 8 as well as the further gradient coils are connected. A radio-frequency transmitter 14 controlled by a process control computer 17 is connected to the whole body antenna 9. The two antennas 9 and 19 are coupled to the process control computer 17 via a signal amplifier 14, a monitor 18 being connected to the process control computer 17 for the display of a tomographic image. The components 14 and 15 form a radio-frequency unit 16 for signal generating and pickup. A radio-frequency shield 20 is provided for decoupling the radio-frequency antennas 9 and 19 from the gradient coil system 7 and 8, this radio-frequency shield 20 being fashioned to conform to a cylindrical surface and being arranged between all coils in the gradient coil system and both radio-frequency antennas 9 and 19. The radio-frequency shield 20 is constructed such that it acts as a shielding essentially only for the high-frequency fields in the megahertz range generated by the antennas. It is transmissive for the low-frequency gradient fields generated by the gradient coils 7 and 8 (and the other gradient coils).

Figure 2:
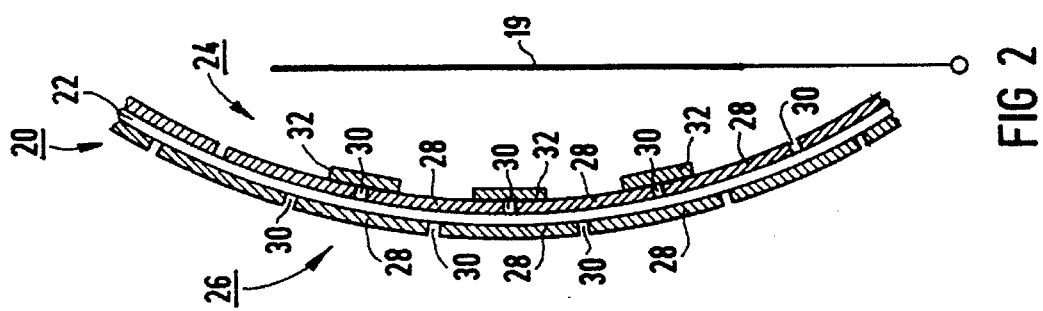
FIG. 2 is a side view of a portion of radio-frequency shielding constructed in accordance with the principles of the present invention.

FIG. 2 then shows a part of the radio-frequency shield 20 in cross section. A dielectric 22, to conform to the cylindrical surface, is the carrier of the radio-frequency shield 20 and is composed, for example, of an epoxy or teflon material (GFK or PTFE material) reinforced with a fiberglass weave. Respective layer arrangements 24 and 26 of copper are applied onto the inside and outside of the dielectric 22. The layer arrangements 24 and 26 have interconnects 28 of equal width that are arranged parallel to one another and are axially aligned and are separated from one another by insulating slots 30. The interconnects 28 and 30 in the first layer arrangement 24 are arranged offset relative to the interconnects 28 and slots 30 of the second layer arrangement 26.

Figure 3:
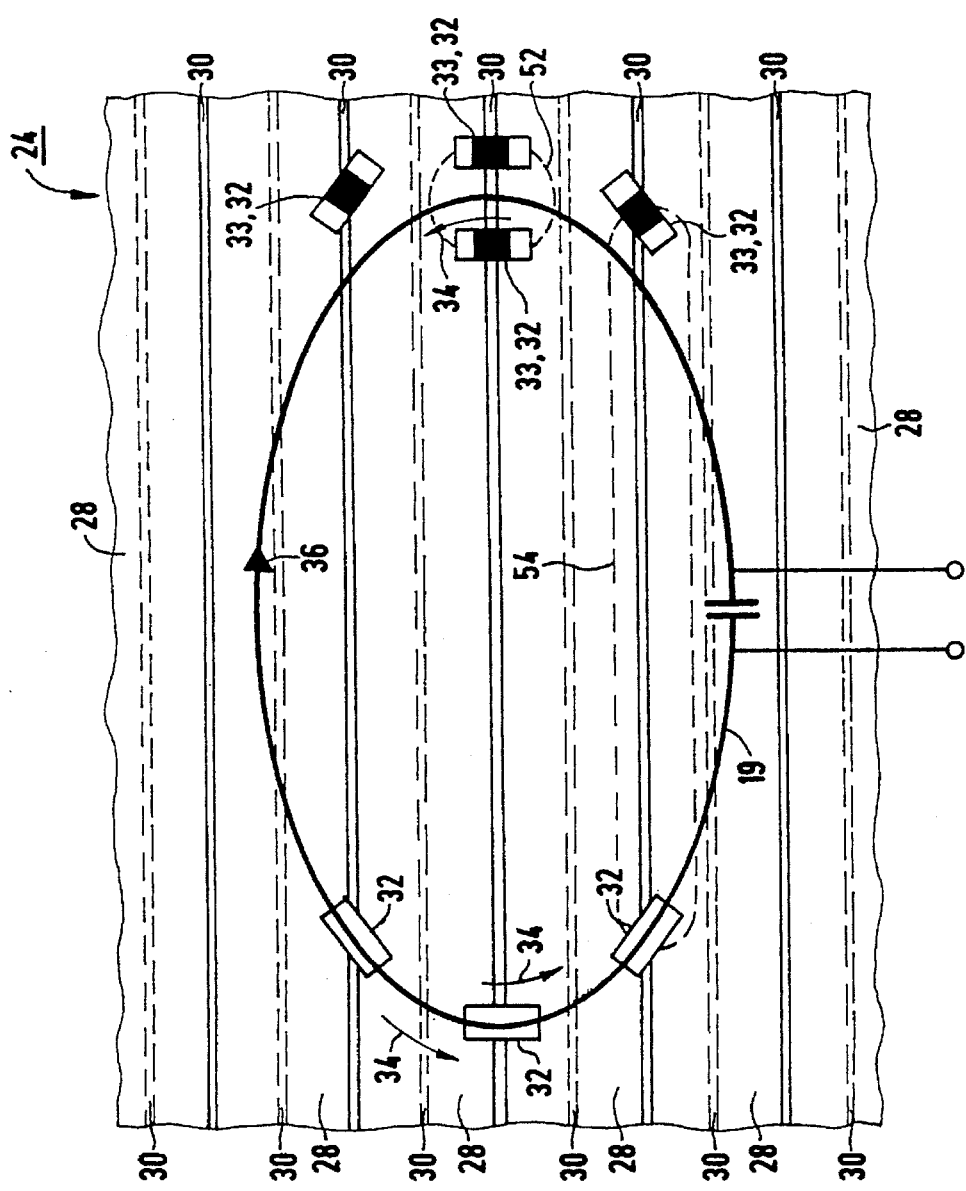
FIG. 3 is a plan view of the inside of the radio-frequency shielding of FIG. 2.

In a plan view, FIG. 3 shows the first film layer arrangement 24, i.e. the inside of the radio-frequency shield 20, in a region wherein the local antenna 19 is arranged. The local antenna 19 is fashioned as a conductor loop and can be employed, for example, for examining the spinal column. Neighboring interconnects 28 in the region of the local antenna 19 are connected to one another via bridges 32 that conduct high-frequency currents. The bridges 32 are thereby arranged such that currents induced in the layer arrangement 24 by the radio-frequency antenna 19—here illustrated by the arrows 34—can flow essentially via the bridges 32 between neighboring interconnects 28. The induced currents 34 flow opposite the current in the antenna 19. The direction of the current in the antenna 19 is illustrated by an arrow 36. Some of the bridges 32 are manufactured of metal foil, these being respectively soldered onto neighboring interconnects 28. In order that the currents induced in the first layer arrangement 24 by the gradient coils 7 and 8 do not encounter any closed current paths via a plurality of interconnects 28, some bridges 32 are implemented as ceramic capacitors 33. The size of the capacitance thereof is selected such that the capacitors 33 offer negligible resistance to the high-frequency current 34 induced by the antennas, whereas the capacitive resistance (impedance) for the currents induced by the gradient coils 7 and 8 is extremely high.

Care is exercised in the arrangement of the bridges 32 and 33 to ensure that no ring currents can flow via a plurality of interconnects 28, the resonant frequency of these ring currents lying in the region of the operating frequency of the magnetic resonance apparatus. The resonant frequency of the ring current 52 indicated by the broken line thus lies significantly below the operating frequency of the magnetic resonance apparatus as a result of the low inductance of the circuit 52. By contrast, the resonant frequency of the circuit indicated by the broken line 54 lies significantly above the operating frequency because of its larger inductance.

Figure 4:
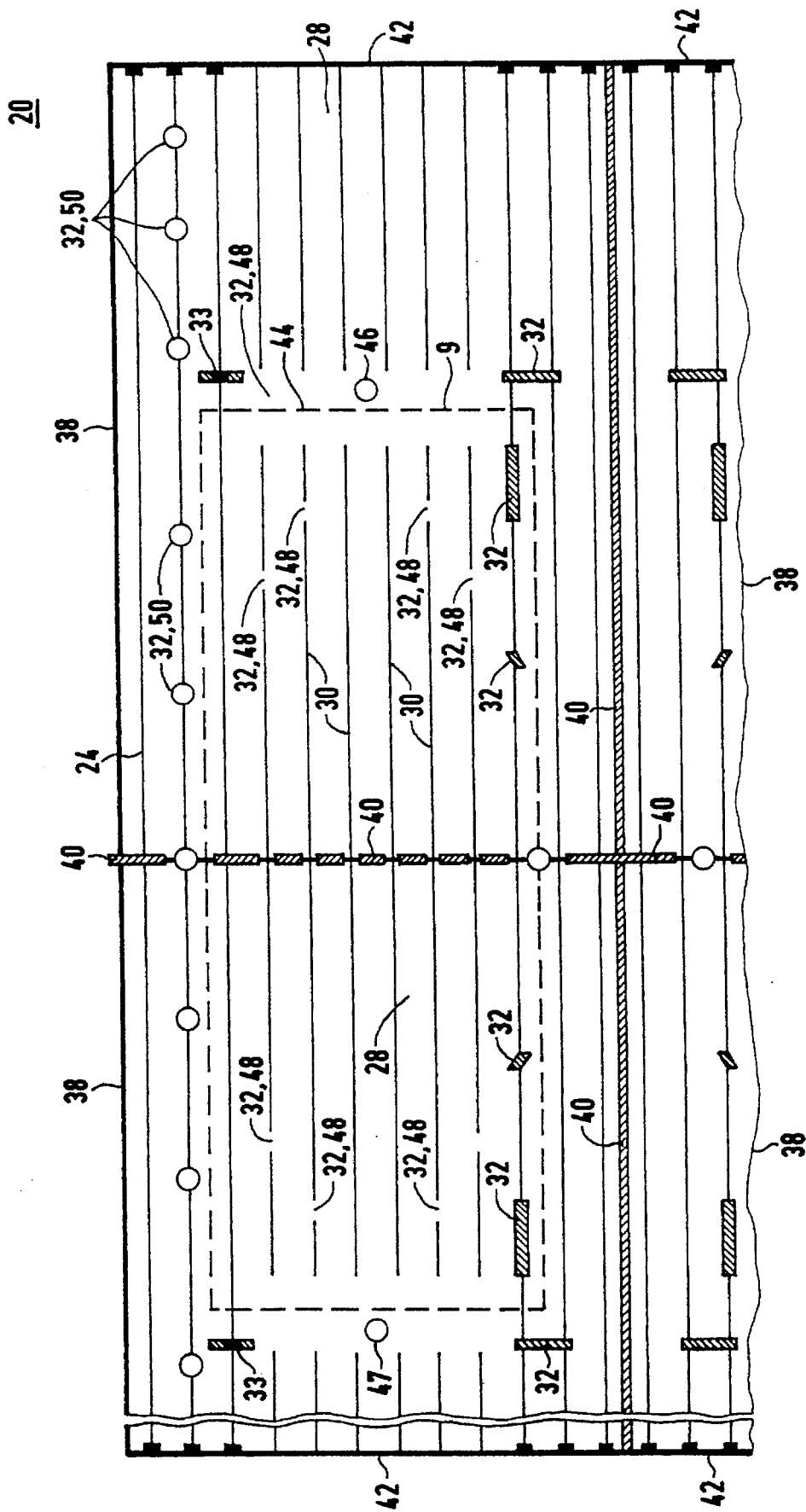
FIG. 4 is a plan view of a further embodiment of radio-frequency shielding constructed in accordance with the principles of the present invention, having bridges constructed differently from the bridges in the embodiment of FIG. 3.

In a developed view, FIG. 4 shows a part of a radio-frequency shield 20 having the shape of a cylindrical surface that is constructed of a number of printed circuit boards 38 electrically connected to one another. FIG. 4 shows a plan view of the first layer arrangement 24 that faces toward the radio-frequency antenna 9. Overall, eight rectangular printed circuit boards 38 are connected to one another via strips 40 of metal foil. The interconnects 28 are in turn arranged on the radio-frequency shield 20 in the longitudinal direction (in z-direction of the coordinate axis 6). A narrow side 42 of a printed circuit board 38 thus covers 90° of the circumference of the generated cylindrical surface. The arrangement of the bridges 32 is adapted here to a whole body antenna 9 of a type disclosed by U.S. Pat. No. 4,506,224. The whole body antenna 9 is formed of four planar sub-antennas 44 that are arranged in the inside of the radio-frequency shield 20 offset by 90° relative to one another. The contour of a sub-antenna 44 is indicated with broken lines in FIG. 4. The planar sub-antennas 44, like the radio-frequency shield 20, can likewise be slotted in the longitudinal direction in order to avoid eddy currents induced by the gradient coil system; this, however, is not shown here. The interconnects that form the sub-antennas 44 are then connected to one another at the ends with bridges, preferably composed of capacitors in the proximity of the feed points 46 and 47 so that the antenna current can flow optimally unimpeded between the interconnects of the sub-antennas 44. The antenna current in the sub-antennas 44 flows in a circuit which is closed via the radio-frequency shield 20. The current direction in the radio-frequency shield 20 is opposite the current direction in the sub-antennas 44, for example from terminal 46 to terminal 47. The bridges 32 are also arranged here such that both the reflected current induced in the radio-frequency shield 20 by the sub-antennas 44 as well as the return antenna current flowing in the radio-frequency shield 20 cannot flow via the dielectric 22, but these currents flow instead directly along the interconnects 28. Again, capacitors 33 are employed as bridges in order to effect a better suppression of eddy currents for the low-frequency gradient currents. Some of the bridges 32, which can be recognized in FIG. 4 as an interruption 44 of the slot 30, are implemented as one piece with the interconnects 28. They can thus already be provided in the printed circuit board layout. Further bridges are implemented as threaded bolts 50 shown as circles. The arrangement of the bridges 32, 33, 48 and 50 is optimized in view of the antenna geometry and in view of the geometry of the gradient coil system.

Although modifications and changes may be suggested by those skilled in the art, it is the intention of the inventors to embody within the patent warranted hereon all changes and modifications as reasonably and properly come within the scope of their contribution to the art.

We claim as our invention:

1. A diagnostic magnetic resonance apparatus comprising:

means for defining an examination space for accepting at least part of an examination subject;

means for generating a basic magnetic field in said examination space;

gradient coil means for generating a plurality of gradient magnetic fields in said examination space superimposed on said basic magnetic field;

radio frequency antenna means for transmitting excitation pulses into said examination subject in said examination space in the presence of said basic magnetic field and said gradient fields, and thereby causing said examination subject to produce magnetic resonance signals, and for receiving said magnetic resonance signals, said radio-frequency antenna means being disposed closer to said examination space than is said gradient coil means; and a radio-frequency shield disposed between said radio-frequency antenna means and said gradient coils means, said radio-frequency shield comprising a first electrically conductive layer and a second electrical conducive layer disposed opposite said first electrical conductive layer, a dielectric disposed between said first and second electrically conductive layers, each of said first and second electrically conductive layers having a plurality of interconnects disposed side-by-side and separated from each other by electrically insulating slots, said slots in the respective first and second electrically conductive layers being disposed offset relative to each other, and adjacent interconnects in at least one of said first and second electrically conductive layers being connected to each other by respective bridges which conduct high-frequency currents, said bridges being disposed in an arrangement preventing inducement of ring currents, having a resonant frequency approximating an operating frequency of the magnetic resonance apparatus, over a plurality of said interconnects, said bridges being disposed on the as least one electrically conductive layer causing currents induced in said at least one electrically conductive layer by said radio-frequency means to flow between said adjacent interconnects substantially only via said bridges.

2. A magnetic resonance diagnostic apparatus as claimed in claim 1, wherein at least some of said bridges comprise pieces of metal foil.

3. A magnetic resonance diagnostic apparatus as claimed in claim 1 wherein at least some of said bridges are formed by capacitors.

4. A magnetic resonance diagnostic apparatus as claimed in claim 1 wherein at least some of said bridges are connected to said interconnects by soldered connections.

5. A magnetic resonance diagnostic apparatus as claimed in claim 1 wherein said first and second electrically conductive layers and said dielectric comprise at least one printed circuit board, and wherein at least some of said bridges are unitarily constructed with said interconnects.

6. A magnetic resonance diagnostic apparatus as claimed in claim 1 wherein said interconnects are disposed parallel to each other.

7. A magnetic resonance diagnostic apparatus as claimed in claim 1 wherein only said one of said electrically conductive layers has said bridges, and wherein said only one electrically conductive layer faces toward said radio-frequency antenna means.

\* \* \* \* \*